(12) United States Patent
Vonk et al.

(10) Patent No.: US 8,340,762 B2
(45) Date of Patent: Dec. 25, 2012

(54) PULSE GENERATION TECHNIQUES FOR IMPLANTABLE PULSE GENERATOR SYSTEMS

(75) Inventors: Ben F. M. Vonk, Wehl (NL); Willem J. A. Esmeijer, Zutphen (NL); Harry B. A. Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 1269 days.

(21) Appl. No.: 10/422,078

(22) Filed: Apr. 23, 2003

(65) Prior Publication Data

US 2004/0215260 A1    Oct. 28, 2004

(51) Int. Cl.
*A61N 1/362* (2006.01)
(52) U.S. Cl. ..................... 607/9; 607/5; 607/4
(58) Field of Classification Search ............ 607/27, 607/28, 13, 4–9
See application file for complete search history.

(56) References Cited

U.S. PATENT DOCUMENTS

| | | | |
|---|---|---|---|
| 4,343,312 A | 8/1982 | Cals et al. | |
| 4,373,531 A * | 2/1983 | Wittkampf et al. | 607/13 |
| 4,811,738 A * | 3/1989 | Economides et al. | 607/13 |
| 4,821,724 A | 4/1989 | Whigham et al. | |
| 4,903,700 A | 2/1990 | Whigham et al. | |
| 4,969,463 A | 11/1990 | Dahl et al. | |
| 5,172,690 A | 12/1992 | Nappholz et al. | |
| 5,330,512 A | 7/1994 | Hauck et al. | |
| 5,741,312 A | 4/1998 | Vonk et al. | |
| 5,766,230 A | 6/1998 | Routh et al. | |
| 5,843,136 A | 12/1998 | Zhu et al. | |
| 5,899,923 A * | 5/1999 | Kroll et al. | 607/5 |
| 5,941,903 A | 8/1999 | Zhu et al. | |
| 5,964,787 A | 10/1999 | Kerver et al. | |
| 6,411,844 B1 * | 6/2002 | Kroll et al. | 607/5 |
| 2003/0014085 A1* | 1/2003 | Prutchi et al. | 607/27 |

* cited by examiner

*Primary Examiner* — Joseph Stoklosa
(74) *Attorney, Agent, or Firm* — Reed A. Duthler; Stephen W. Bauer

(57) ABSTRACT

The invention is directed to tri-phasic pulse generation techniques that make use of a pre-stimulus phase, a stimulus phase, and a post-stimulus phase in a pulse generation cycle. During the pre-stimulus phase, an output capacitor is charged to a desired voltage level. During the stimulus phase, the capacitor is discharged, and during the post-stimulus phase recharging of the capacitor begins again. In accordance with the invention, charging of the output capacitor can be terminated during the post-stimulus phase after a measured voltage in the patient is greater than or equal to a threshold.

15 Claims, 4 Drawing Sheets

PULSE GENERATION TECHNIQUES FOR IMPLANTABLE PULSE GENERATOR SYSTEMS

FIELD OF THE INVENTION

The invention relates to implantable medical devices, and more particularly to implantable pulse generator (IPG) systems that deliver therapeutic stimulation pulses to a patient.

BACKGROUND OF THE INVENTION

A wide variety of medical devices have been developed in order to deliver stimulation therapy to the patient. An implantable pulse generator (IPG) system generally refers to a medical device that delivers pulses of therapeutic stimulation to a patient. IPG systems include an IPG device and one or more implantable medical leads coupled to the IPG device. The IPG device comprises a housing that houses circuitry for the generation of therapeutic stimulation pulses, and the leads position electrodes within the patient at locations desirable for delivery of the stimulation pulses. The IPG device is typically a biocompatible hermetically sealed structure that, like the leads, is implanted in the patient. However, in some cases, only the leads are implanted, and the IPG device resides at a location external to the patient.

One common example of an IPG device is a pacemaker. A pacemaker system typically includes a pacemaker device and one or more pacing and sensing leads for delivery of pacing pulses to a patient's heart. Another example of an IPG device is a combination pacemaker-cardioverter-defibrillator. Other examples include implantable brain stimulators, implantable gastric system stimulators, implantable nerve stimulators or muscle, stimulators, implantable lower colon stimulators, and so on.

Tri-phasic pulse generation refers to a pulse generation technique that uses three phases in a pulse generation cycle. In particular, tri-phasic pulse generation involves a pre-stimulus phase, a stimulus phase, and a post-stimulus phase. During the pre-stimulus and post-stimulus phases an output capacitor is charged, whereas during the stimulus phase the output capacitor is discharged to deliver the stored charge to the patient as a stimulation pulse. More specifically, during the pre-stimulus phase, the output capacitor is charged to a desired voltage level for stimulation, during the stimulus phase, the capacitor is discharged, and during the post-stimulus phase recharging of the capacitor begins anew.

BRIEF SUMMARY OF THE INVENTION

In general, the invention is directed to tri-phasic pulse generation techniques that make use of a pre-stimulus phase, a stimulus phase, and a post-stimulus phase in a pulse generation cycle. During the pre-stimulus phase, an output capacitor is charged to a desired voltage level. During the stimulus phase, the capacitor is discharged, and during the post-stimulus phase recharging of the capacitor begins again. In accordance with the invention, charging of the output capacitor can be terminated during the post-stimulus phase after a measured voltage in the patient is greater than or equal to a threshold. The threshold may define a zero voltage value, e.g., ground potential, or may be slightly below or above zero voltage to account for residual charging or discharging effects. In either case, tri-phasic pulse generation may be improved by more quickly identifying a desired voltage in the patient, i.e., zero voltage, at the end of the tri-phasic cycle. The zero voltage may correspond to a substantially uncharged or unpolarized state at the location where the stimulus pulses are delivered.

In one embodiment, the invention provides a method comprising charging a capacitor of a implantable pulse generator system during a pre-stimulus phase and discharging the capacitor to stimulate a patient during a stimulus phase that follows the pre-stimulus phase. The method may further comprise charging the capacitor during a post-stimulus phase that follows the stimulus phase, and terminating the charging of the capacitor during the post-stimulus phase after a measured voltage in the patient is greater than or equal to a threshold.

In another embodiment, the invention provides an implantable pulse generator system comprising an implantable pulse generator device and one or more implantable leads coupled to the implantable pulse generator device to position electrodes within a patient. The system may include a stimulation capacitor to deliver tri-phasic stimulation pulses to a patient via the leads, and a voltage detector to measure voltage within the patient at a location where the tri-phasic stimulation pulses are delivered to the patient. The system may also include circuitry to control charging and discharging of the stimulation capacitor by charging the capacitor during a pre-stimulus phase, discharging the capacitor to stimulate the patient during a stimulus phase that follows the pre-stimulus phase, charging the capacitor during a post-stimulus phase that follows the stimulus phase, and terminating the charging of the capacitor during the post-stimulus phase after a measured voltage of the voltage detector is greater than or equal to a threshold.

In another embodiment, the invention provides a circuit for an implantable pulse generator, the circuit being configured to control charging and discharging of a stimulation capacitor by charging the capacitor during a pre-stimulus phase, discharging the capacitor to stimulate a patient during a stimulus phase that follows the pre-stimulus phase, charging the capacitor during a post-stimulus phase that follows the stimulus phase, and terminating the charging of the capacitor during the post-stimulus phase after a measured voltage within the patient is greater than or equal to a threshold.

In another embodiment, the invention provides an apparatus comprising means for charging a capacitor of a implantable pulse generator system during a pre-stimulus phase and means for discharging the capacitor to stimulate a patient with implantable pulse generator system during a stimulus phase that follows the pre-stimulus phase. The apparatus may further comprise means for charging the capacitor during a post-stimulus phase that follows the stimulus phase, and means for terminating the charging of the capacitor during the post-stimulus phase after a measured voltage in the patient is greater than or equal to a threshold.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
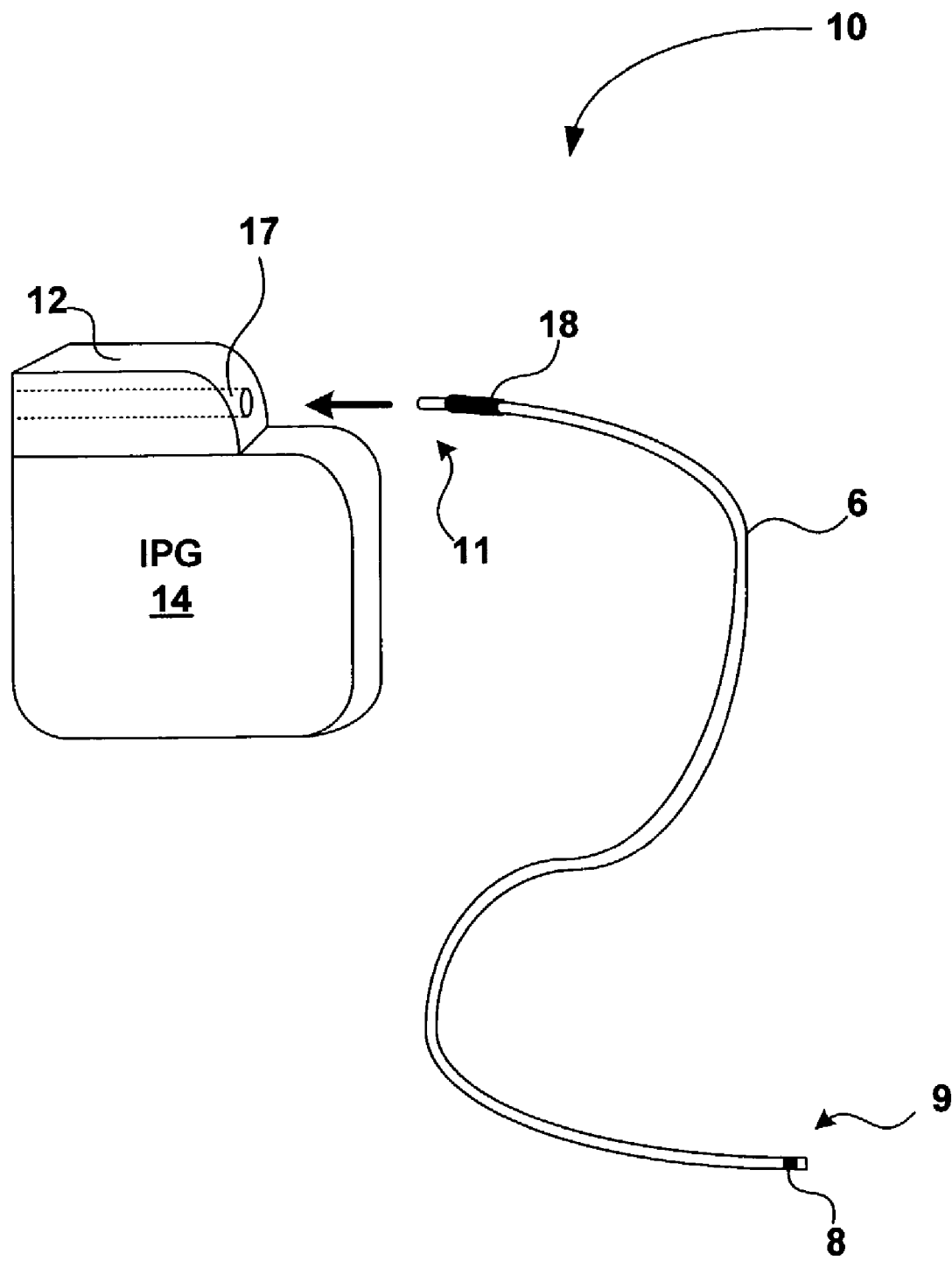
FIG. 1 is a schematic view of an implantable pulse generator (IPG) system comprising an IPG and one or more implantable leads.

The invention is directed to tri-phasic pulse generation techniques for use in implantable pulse generators (IPGs) such as cardiac pacemakers, and the like. The tri-phasic pulse generation techniques make use of a pre-stimulus phase, a stimulus phase, and a post-stimulus phase in order to achieve a substantially zero overall charge transfer to the stimulated site over the course of a pulse generation cycle. During the post-stimulus and the pre-stimulus phase, an output capacitor is charged to a desired voltage level. During the stimulus phase, the capacitor is discharged to provide a stimulation pulse. Essential to the tri-phasic pulse generation technique is that the output capacitor is only partially charged during the post-stimulus phase, in order to obtain a zero voltage change over the heart at the end of the tri-phasic cycle with respect to the voltage over the heart just before the tri-phasic cycle. Such partial charging during the post-stimulus phase can also result in no voltage change over the heart in the period immediately after the tri-phasic pulse. A voltage change is also referred to as "polarization." The total of post-stimulus phase and pre-stimulus phase charging can achieve a substantially zero overall charge transfer to the stimulated site.

In accordance with the invention, charging of the output capacitor can be terminated during the post-stimulus phase after a measured voltage in the patient is greater than or equal to a threshold. The threshold may define a zero voltage value indicating that the tissue being stimulated is substantially unpolarized. Alternatively, the threshold may be slightly below or above a zero voltage in order to account for residual charging effects, e.g., charging that occurs during or following the time measurements are taken. Alternatively, the threshold may be set to a programmable level, and may be selected to account for differences in dynamic behavior of the leads and effects at the lead/tissue interface. In any case, tri-phasic pulse generation may be improved by more quickly identifying a desired voltage in the patient, e.g., a zero voltage, following the tri-phasic cycle. For example, such techniques can reduce the time interval associated with the post-stimulus phase, allowing sensing electrodes to be enabled more quickly following the stimulus phase. In other words, blanking of sensing capabilities can be terminated more quickly in the IPG. In some cases, such early termination of blanking can allow for detection of an evoked response to the stimulation.

Charging of the output capacitor during the pre-stimulus and post-stimulus phases may occur in discrete charging intervals. The discrete charging intervals may be separated by intervals in which charging does not occur. Accordingly, during the post-stimulus phase, voltage measurements within the patient can be made between discrete charging intervals. Once the voltage within the patient reaches a defined threshold, such as zero voltage, the post-stimulus phase can be terminated. Then, blanking can be terminated to allow for detection of an evoked response to the stimulation, which typically occurs within 50 milliseconds of the delivery of stimulation. In this manner, tri-phasic pulse generation can be improved.

FIG. 1 is a schematic view of an IPG system 10 comprising an IPG 14 and one or more implantable leads 6. A distal end 9 of implantable lead 6 includes an electrode 8 for delivering stimulation pulses to an implanted location within a patient. Distal end 9 of implantable lead 6 is implanted at the desired location, such as within a heart chamber, and a proximal end 11 of lead 6 is coupled to IPG 14. For example, proximal end 11 of lead 6 may be inserted into channel 17 of connector module 12 so that electrical interface 18 of lead 6 is electrically coupled to circuitry of IPG 14. In particular, connector module 12 forms part of IPG 14 and may be electrically coupled to sensing circuitry and/or stimulation circuitry within IPG 14.

Implantable lead 6 may include any number of additional electrodes (not shown) distributed along the length of lead. Electrode 8 or other electrodes may be used for sensing, delivery of stimulation pulses, or possibly the delivery of high voltage shocks to a patient. Electrode 8 as well as other electrodes (if desired) can be made from an electrically conductive, biocompatible material such as elgiloy, platinum, platinum-iridium, platinum-iridium oxide, sintered platinum powder or other residue product after combustion with some high heat source, platinum coated with titanium-nitride, pyrolytic carbon, or the like. Electrode 8 is electrically coupled to one or more conductive filars that extend along the body of lead 6, e.g., in a coiled construction. Electrode 8 may be electrically coupled to electrical interface 18 via the filars that extend along the body of lead 6. Although a single lead 6 is shown for purposes of illustration, any number of leads may be used in system 10, and thus coupled to connector module 12 of IPG 14.

Electrode 8 may form a substantially cylindrical ring of conductive material that extends about an exterior wall of lead 6. For example, electrode 8 may extend the entire 360 degrees about lead 6, or to some lesser extent. In some embodiments, lead 6 may be tubular but not necessarily cylindrical. For example, electrode 8 and lead 6 may have alternative cross sections, e.g., square, rectangular, hexagonal, oval or the like. In any case, electrode 8 may be coupled to one or more electrically conductive filars that extend along the length of lead 6. The filars are typically coiled to define a lumen of lead 6.

IPG 14 comprises any device capable of delivering stimulation pulses to a patient. For example, IPG 14 may take the form of an implantable cardiac pacemaker, a combination pacemaker-cardioverter-defibrillator, or the like. The invention, however, is not limited for use with cardiac pacing, but may find wide applicability with any IPG that delivers therapeutic pulses to any location within a patient. For example, the invention may find use with a neurological device such as a deep-brain stimulation device or a spinal cord stimulation device. In those cases, the leads may be stereotactically probed into the brain to position electrodes for deep brain stimulation, or into the spine for spinal stimulation. In other applications, invention may be used with muscular stimulation devices, gastric system stimulation devices, nerve stimulation devices, lower colon stimulation devices, or the like. In short, tri-phasic pulse generation techniques, described herein, may find useful applications in a wide variety IPG systems. For purposes of example, in the description that follows, tri-phasic pulse generation techniques are described as being applied to a patient's heart, e.g., for cardiac pacing.

Figure 2:
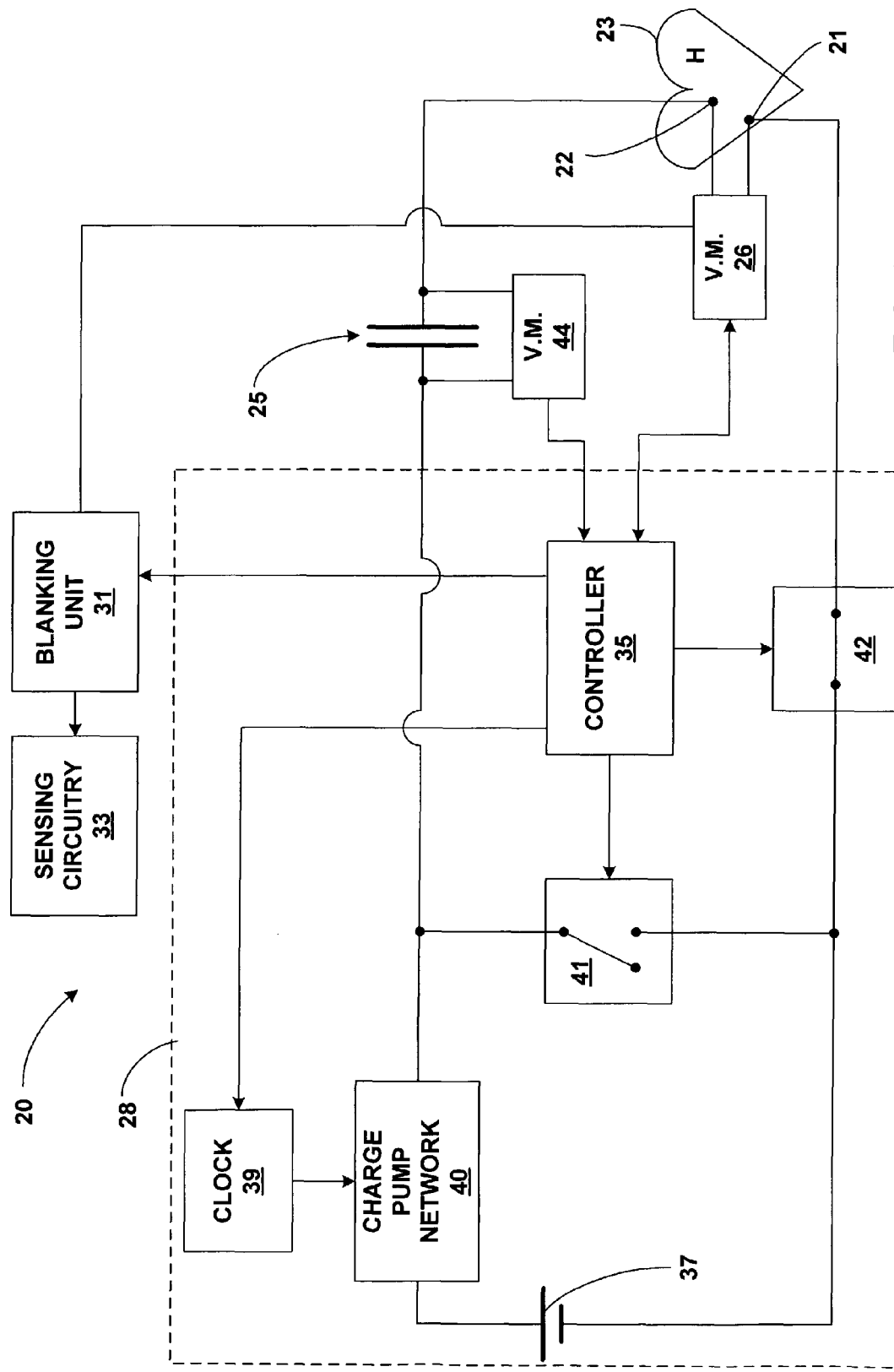
FIG. 2 is a block diagram of an exemplary IPG system in the form a cardiac pacemaker.

FIG. 2 is a block diagram of an exemplary IPG system 20 in the form of a cardiac pacemaker. System 20 may correspond to system 10 of FIG. 1. In general, IPG system 20 comprises an IPG device that includes the various circuitry components illustrated in FIG. 2 and one or more leads (not illustrated) coupled to the circuitry to position two or more sensing or stimulation electrodes 21, 22 with respect to heart 23. In some cases, one of electrodes 21, 22 can be positioned in the heart and the other of electrodes 21, 22 can comprise a reference electrode, possibly within the housing of IPG 14 (FIG. 1).

System 20 includes a stimulation capacitor 25 to deliver tri-phasic stimulation pulses to heart 23 via a lead (not shown in FIG. 2) that positions electrode 21 with respect to heart 23. System 20 also includes a voltage detector such as volt meter (V.M.) 26 to measure the voltage across heart 23. In addition, system 20 includes circuitry 28 to control charging and discharging of stimulation capacitor 25 by charging capacitor 25 during a pre-stimulus phase, discharging capacitor 25 to stimulate heart 23 during a stimulus phase that follows the pre-stimulus phase, charging capacitor 25 during a post-stimulus phase that follows the stimulus phase, and terminating the charging of capacitor 25 during the post-stimulus phase after a measured voltage of volt meter 26 is greater than or equal to a threshold.

Again, the threshold may define a zero voltage value, or may be slightly below or above a zero voltage to account for residual charging or discharging effects. In other words, it may be desirable to set the threshold slightly below or above zero, so that upon detection of the threshold and termination of the charging, residual charging or discharging during or following the time when the measurement was taken will change the voltage on heart 23 to approximately zero so that the heart is substantially unpolarized. The threshold may be within 100 mV of zero voltage, and typically within 10 mV of zero voltage, although the invention is not necessarily limited in that respect.

In any case, tri-phasic pulse generation may be improved because system 20 quickly identifies a desired voltage of heart 23, such as zero voltage, during the post-stimulus phase of the tri-phasic cycle. Accordingly, system 20 can reduce the time interval associated with the post-stimulus phase, allowing sensing electrode 22 to be enabled more quickly following the stimulus phase. In other words, blanking unit 31 can terminate blanking of sensing circuitry 33 of system 20 shortly after volt meter 26 identifies that the voltage across heart 23 has reached the threshold. For example, blanking unit 31 may terminate blanking of sensing circuitry 33 within a period of a few milliseconds after volt meter 26 identifies that the voltage across heart 23 has reached the threshold. Such early termination of blanking by blanking unit 31 may allow sensing circuitry 33 to detect an evoked response to the stimulation, which typically occurs within 50 milliseconds following the delivery of stimulation, although the invention is not limited in that respect. Detection of an evoked response is very useful, and can result in stimulation at an energy level just high enough to let the tissue respond to the stimulation, thus reducing power consumption of the IPG. Also, the possibility of detection of an evoked response with a very short blanking period can improve the sensing capabilities of the IPG, thus opening possibilities for improvement of IPG delivered therapy.

A wide variety of circuit configurations may be implemented to achieve tri-phasic pulse generation according to the invention. Circuitry 28 is only one example of a circuit that controls charging and discharging of stimulation capacitor 25. In this example, circuitry 28 includes a controller 35, such as a microprocessor, a digital signal processor (DSP) executing software, an application specific integrated circuit (ASIC), a field programmable gate array, discrete logic components, or the like, for controlling the charging and discharging process of capacitor 25. Circuitry 28 also includes a power source 37 such as a battery to provide the energy used to charge capacitor 25.

Controller 35 provides control signals to clock circuit 39 to activate and control charge pump network 40, which may comprise a set of switches that cause capacitor charging to occur in discrete charge intervals as described in greater detail below. Controller 35 also provides control signals to switches 41 and 42 to switch between the various phases of the tri-phasic pulse generation cycle. Switch 42 may comprise an activation switch for activating the pulse generation cycle. Switch 41 may comprise a switch for changing between the pre-stimulus phase, the stimulus phase, and the post-stimulus phase.

To initiate the pulse generation cycle, controller 35 provides control signals to close switch 42. In addition, controller 35 provides control signals to open switch 41 for the pre-stimulus phase, and also provides control signals to clock circuit 39 which activates and controls charge pump network 40. Power source 37 provides power to charge pump network 40, which is clocked to charge capacitor 25 in discrete charging intervals. Each discrete charging interval is followed by an interval in which no charging occurs. Control signals from controller 35 to clock circuit 39 may enable such clocking of switches in charge pump network 40 so that charging of capacitor 25 occurs in discrete intervals.

During the pre-stimulus phase, capacitor 25 is charged in the discrete intervals until a voltage detector such as volt meter 44 detects that capacitor 25 is properly charged. Such charging of capacitor 25 also creates a charge on heart 23. Controller 35 may receive signals from volt meter 44 indicating that capacitor 25 is properly charged, and in response may send control signals for the stimulus phase. In particular, controller 35 sends control signals to close switch 41, which creates an electrical path for discharge capacitor 25 across heart 23.

When controller 35 closes switch 41 for the stimulus phase, capacitor 25 is discharged to provide a pacing pulse to heart 23, e.g., at electrode 21. Then, following discharge of capacitor 25, controller opens switch 41 to enter the post-stimulus phase of the pulse generation cycle. The post-stimulus phase is similar to the pre-stimulus phase, in that capacitor 25 is charged in the discrete intervals. Such tri-phasic pulse generation techniques making use of a pre-stimulus phase, a stimulus phase, and a post-stimulus phase, can achieve a substantially zero overall charge transfer to heart 23 over the course of a pulse generation cycle. In other words, the charge transferred to heart 23 during the pre-stimulus and post-stimulus phases can negate the charge transferred to heart 23 during the stimulus phase so that following the pulse generation cycle, heart 23 is substantially uncharged. Put another way, following the cycle, heart 23 can return to its intrinsic state, e.g., being substantially unpolarized.

When controller 35 initiates the pulse generation cycle, e.g., by providing control signals to switches 41, 42 and clock 39, it may also provide control signals to blanking unit 31. Blanking unit 31 controls the blanking of sensing circuitry 33, which is coupled to one or more sensing electrodes 22. Sensing electrode 22 may comprise the same electrode used for stimulation, or may comprise a separate electrode used specifically for sensing. In any case, during the pulse generation cycle, blanking unit 31 disables sensing circuitry 33 so that electrical events are not sensed during the pulse generation cycle. For example, blanking unit 31 may cause one or more sensing amplifiers of sensing circuitry 33 to be disabled, or blanking unit 31 can block any signals coming from heart 23 during the blanking period. In either case, if an electrical event occurs during this blanking period, the event will not be sensed by sensing circuitry 33.

In accordance with the invention, system 20 includes a voltage detector, such as volt meter 26 positioned to detect the voltage across heart 23. In particular, during the post-stimulus interval, volt meter 26 provides voltage measurements of heart 23 to controller 35. Controller 35 may specifically invoke volt meter 26 during the intervals between the discrete charging intervals. Upon receiving voltage measurements of heart 23, controller 35 compares the voltage measurements to a threshold, and terminates the post-stimulus interval once the measured voltage associated with heart 23 reaches that threshold.

The threshold may define a zero voltage value, or may be slightly below or above a zero voltage to account for residual charging or discharging effects. In other words, it may be desirable to set the threshold slightly below or above zero, so that upon detection of the threshold and termination of the charging, residual charging or discharging during or following the termination will raise or lower the voltage on the heart to be approximately zero voltage. In either case, tri-phasic pulse generation may be improved because controller 35 can more quickly detect when heart 23 is at the desired voltage, e.g., zero. Accordingly, such techniques can reduce the time interval associated with the post-stimulus phase, allowing sensing circuitry 33 to be enabled more quickly following the stimulus phase. For example, once controller 35 terminates the post-stimulus interval upon determining that the voltage on heart 23 has reached the defined threshold, controller 35 can send signals to blanking unit 31 to terminate the blanking of sensing circuitry 33. Thus, following stimulation, blanking may be terminated more quickly, possibly allowing sensing circuitry 33 to sense an evoked response, which typically occurs within 50 milliseconds of the delivery of stimulation.

In some cases, the threshold or thresholds applied by controller 35 can be programmable. Also, system 20 may operate such that once the detection that the measured voltage has crossed the threshold voltage, one or more additional discrete charge cycles (pump cycles) are given, after which the post-stimulus period is ended. Such an "anticipating" detection method can block circumvention of the patent and may be extended to allow for one or more discrete charge cycles after the threshold crossing. In addition, in order to avoid other possibilities of circumventing the patent, controller 35 may estimate the proper moment to terminate the post-stimulus phase, based on the trend seen in subsequent measurements of the voltage over heart 23. In other words controller 35 may adapt termination of the post-stimulus phase based on the results of previous charge cycles. In yet other cases, controller 35 identifies measured voltage over heart 23 between the discrete charge cycles to determine the proper moment for terminating the post-stimulus period, or to obtain minimal voltage changes over the heart immediately after the post-stimulus, thus minimizing polarization of heart 23.

Although details of FIG. 2 are provided in the context of cardiac pacing in which pulses are delivered to heart 23, the invention can be used in any of a number of other implantable pulse generator systems. In general, a voltage detector is used to measure voltage within the patient at a location where the tri-phasic stimulation pulses are delivered to the patient. The circuitry that controls charging and discharging of the stimulation capacitor can terminate the charging of the capacitor during the post-stimulus phase after a measured voltage of the voltage detector is greater than or equal to a threshold. The location where the tri-phasic stimulation pulses are delivered may correspond to the patient's heart, but the invention is not limited in that respect.

Figure 3:
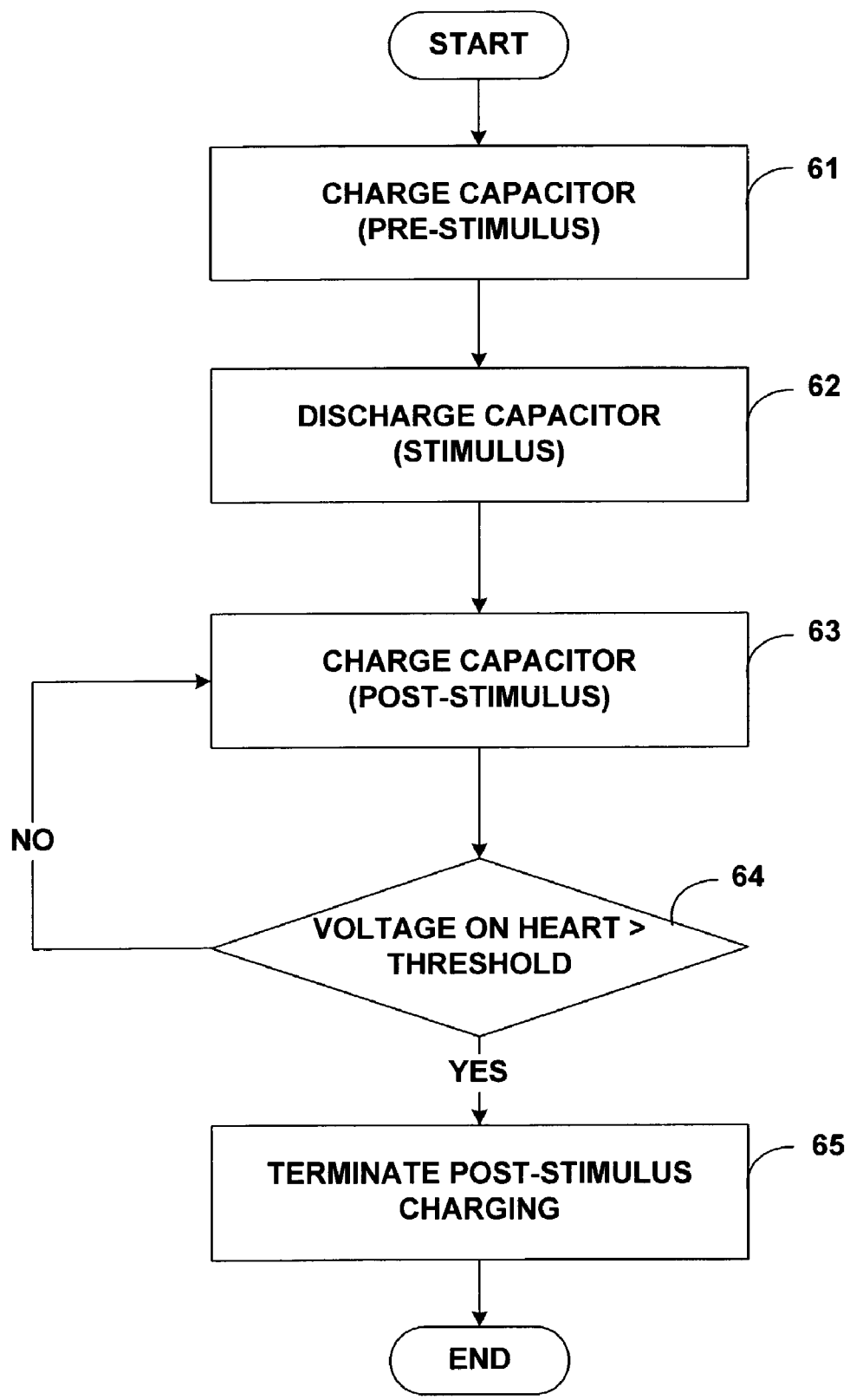
FIG. 3 is a flow diagram according to an embodiment of the invention.

FIG. 3 is a flow diagram according to an embodiment of the invention. As shown in FIG. 3, circuitry 28 charges capacitor 25 during a pre-stimulus phase (61), which may involve charging capacitor 25 in discrete charge intervals. For example, a voltage detector such as volt meter 44 across capacitor 25 can identify when capacitor 25 is adequately charged for delivery of the stimulus pulse. Circuitry 28 then causes discharge of capacitor 25 during a stimulus phase (62). Following delivery of the stimulus, circuitry 28 begins charging capacitor 25 during a post-stimulus phase (63), which may also involve charging capacitor 25 in discrete charge intervals.

During the post-stimulus phase a voltage detector such as volt meter 26 across heart 23 can identify when the voltage on heart 23 has reached a defined threshold (64). In other words, during the post-stimulation phase volt meter 26 can measure the polarization artifacts on heart 23, as a result of the stimulation. Once the voltage on heart 23 has reached the defined threshold (yes branch of 64), circuitry 28 terminates the post-stimulus charging of capacitor 25 (65). If desired, blanking can be likewise terminated once the voltage on heart 23 has reached the defined threshold. Accordingly, sensing circuitry 33 may be able to sense an evoked response to stimulation of heart 23.

Figure 4:
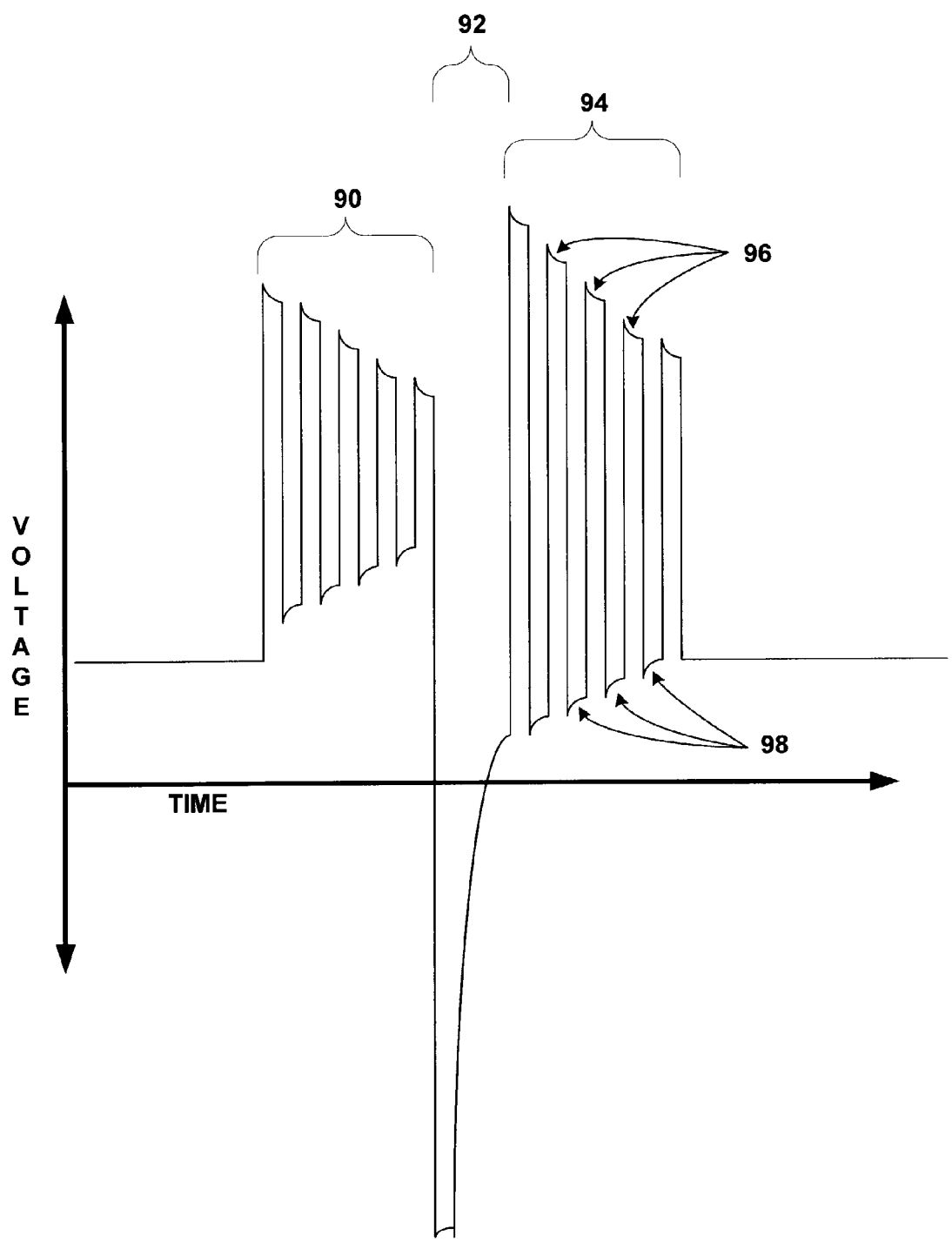
FIG. 4 is a conceptual graph illustrating output pulses during tri-phasic pulse generation cycle according to an embodiment of the invention.

FIG. 4 is a conceptual graph illustrating output pulses during tri-phasic pulse generation cycle according to an embodiment of the invention. Capacitor 25 is charged in discrete charging intervals during a pre-stimulus phase 90. Capacitor 25 is discharged during the stimulus phase 92, and capacitor is re-charged in discrete charging intervals during a post-stimulus phase 94. Such discrete charging allows for measurements of the voltage of heart 23 to be made between the intervals. For example, during the post-stimulation phase 94, charging may occur during time intervals 96. Measurements of the voltage of heart 23 are made between the charging intervals, e.g., during time intervals 98. For example, controller 35 may invoke volt meter 26 specifically during time intervals 98 so that measurements of the voltage of heart 23 can be obtained for comparison to the threshold.

A number of embodiments of the invention have been described. However, one skilled in the art will appreciate that the invention can be practiced with embodiments other than those disclosed. For example, although various details of the invention have been provide in the context of cardiac pacing, the same principles may be applied whenever tri-phasic pulse generation is used, e.g., in other locations within a patient. In general, a voltage detector is used to measure voltage within the patient at a location where the tri-phasic stimulation pulses are delivered to the patient. The circuitry that controls charging and discharging of the stimulation capacitor can terminate the charging of the capacitor during the post-stimulus phase after a measured voltage of the voltage detector is greater than or equal to a threshold. Additional techniques may also be employed to allow for one or more charge cycles after the detection moment, or to adapt termination of the charging based on trends or predictions.

Also, although various techniques have been described with reference to circuitry 28, numerous other implementations of circuitry could be used in which the circuitry controls charging and discharging of the stimulation capacitor by charging the capacitor during a pre-stimulus phase, discharging the capacitor to stimulate the patient during a stimulus phase that follows the pre-stimulus phase, charging the capacitor during a post-stimulus phase that follows the stimulus phase, and terminating the charging of the capacitor during the post-stimulus phase after a measured voltage of the voltage detector is greater than or equal to a threshold. For example, the invention may be implemented in hardware, software, firmware, or the like.

Example hardware implementations of control unit 35 include implementations within an application specific integrated circuit (ASIC), a field programmable gate array (FPGA), a programmable logic device, specifically designed hardware components, one or more processors, or any combination thereof. If implemented in software, a computer readable medium may store computer readable instructions, e.g., program code, that can be executed by a processor or DSP to carry out one or more of the techniques described above. For example, the computer readable medium may comprise random access memory (RAM), read-only memory (ROM), non-volatile random access memory (NVRAM), electrically erasable programmable read-only memory (EEPROM), flash memory, or the like. The computer readable medium may comprise computer readable instructions that when executed in an IPG to carry out one or more of the techniques described herein. The disclosed embodiments are presented for purposes of illustration and not limitation, and the invention is limited only by the claims that follow.

What is claimed is:

1. A method of delivering stimulation pulses to patient tissue, the method comprising:
charging a capacitor of an implantable pulse generator system during a pre-stimulus phase;
discharging the capacitor to stimulate patient tissue during a stimulus phase that follows the pre-stimulus phase;
charging the capacitor during a post-stimulus phase that follows the stimulus phase in discrete charging intervals;
taking voltage measurements, during the post-stimulus phase in intervals in which charging does not occur, across the patient tissue where the stimulation pulses are delivered; and
terminating the charging of the capacitor during the post-stimulus phase responsive to the measured voltage across the patient tissue being greater than or equal to a threshold.

2. The method of claim 1, further comprising measuring the voltage during the post-stimulus phase between the discrete charging intervals of the post-stimulus phase.

3. The method of claim 2, wherein discharging the capacitor to stimulate the patient tissue comprises stimulating the patient's heart and wherein measuring the voltage across the patient comprises measuring a voltage between two locations on of the patient's heart.

4. The method of claim 1, wherein the threshold defines a zero voltage value.

5. The method of claim 1, further comprising:
blanking sensing capabilities of the implantable pulse generator system prior to the pre-stimulus phase; and
terminating the blanking after the measured voltage in the patient is greater than or equal to the threshold.

6. The method of claim 5, further comprising sensing an evoked response following terminating the blanking of the implantable pulse generator system.

7. The method of claim 5, wherein terminating the blanking of the implantable pulse generator system occurs within 50 milliseconds after discharging the capacitor to stimulate the patient.

8. The method of claim 1, wherein the implantable pulse generator system comprises a cardiac pacemaker.

9. An implantable pulse generator, comprising:
a capacitor;
circuitry charging the capacitor during a pre-stimulus phase;
circuitry discharging the capacitor to stimulate patient tissue during a stimulus phase that follows the pre-stimulus phase;
circuitry re-charging the capacitor during a post-stimulus phase that follows the stimulus phase in discrete charging intervals;
circuitry measuring a voltage across the patient tissue during the post-stimulus phase in intervals in which charging does not occur; and
circuitry terminating the charging of the capacitor during the post-stimulus phase responsive to the measured voltage across the patient tissue, which measurement is taken during the post-stimulus phase, being greater than or equal to the threshold.

10. The implantable pulse generator of claim 9, wherein the threshold defines a zero voltage value.

11. The implantable pulse generator of claim 9 wherein the circuitry measuring the voltage across the patient tissue is specifically invoked during intervals between the discrete charging intervals.

12. An apparatus comprising:
means for charging a capacitor of an implantable pulse generator system during a pre-stimulus phase;
means for discharging the capacitor to stimulate patient tissue during a stimulus phase that follows the pre-stimulus phase;
means for re-charging the capacitor during a post-stimulus phase that follows the stimulus phase in discrete charging intervals;
means for measuring a voltage across the patient tissue during the post-stimulus phase in intervals in which charging does not occur; and
means for terminating the charging of the capacitor during the post-stimulus phase when a measured voltage across the patient tissue, taken during the post-stimulus phase, is greater than or equal to a threshold.

13. The apparatus of claim 12, further comprising means for measuring the voltage across the patient tissue during the post-stimulus phase between the discrete charging intervals.

14. The apparatus of claim 12, further comprising:
means for blanking the implantable pulse generator system prior to the pre-stimulus phase; and
means for terminating blanking of the implantable pulse generator system after the measured voltage in the patient is greater than or equal to the threshold.

15. The apparatus of claim 14, further comprising means for sensing an evoked response following terminating blanking of the implantable pulse generator system.

* * * * *